United States Patent [19]

Morris

[11] Patent Number: 4,583,572

[45] Date of Patent: Apr. 22, 1986

[54] SHIELD FOR LIQUID SAMPLE CONTAINER

[76] Inventor: Randy A. Morris, 724 Abney St., St. Albans, W. Va. 25177

[21] Appl. No.: 630,758

[22] Filed: Jul. 13, 1984

[51] Int. Cl.$^4$ ................................................ B65B 3/04
[52] U.S. Cl. ..................................... 141/97; 141/285; 141/392
[58] Field of Search ........................... 141/1-12, 141/37-66, 97, 285-310, 392

[56] References Cited

U.S. PATENT DOCUMENTS

| | | | |
|---|---|---|---|
| 1,113,582 | 10/1914 | Schroeder | 141/392 |
| 2,058,118 | 10/1936 | White | 141/392 |
| 3,295,563 | 1/1967 | Laya et al. | 141/97 |
| 3,933,186 | 1/1976 | Sheffler | 141/97 |
| 3,935,886 | 2/1976 | Duncan | 141/392 |
| 4,010,781 | 3/1977 | Sutcliffe | 141/392 |
| 4,151,867 | 5/1979 | Wilhere | 141/291 |

Primary Examiner—Houston S. Bell, Jr.
Attorney, Agent, or Firm—Donald A. Kettlestrings

[57] ABSTRACT

A safety shield for a liquid sample container, the shield comprising a nozzle adapted to be connected in fluid communication with a source of the liquid, a housing defining a lower open end and in operative relationship with the nozzle for partially enclosing the nozzle, and an assembly in operative relationship with the nozzle and with the housing for directing in a downward direction any of the liquids splashed or overflowed from the container and any vapors from the liquid.

11 Claims, 6 Drawing Figures

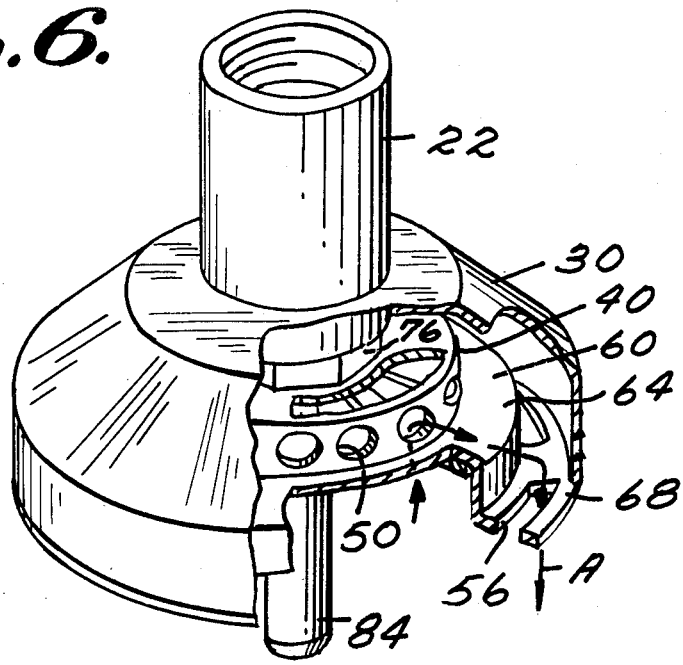
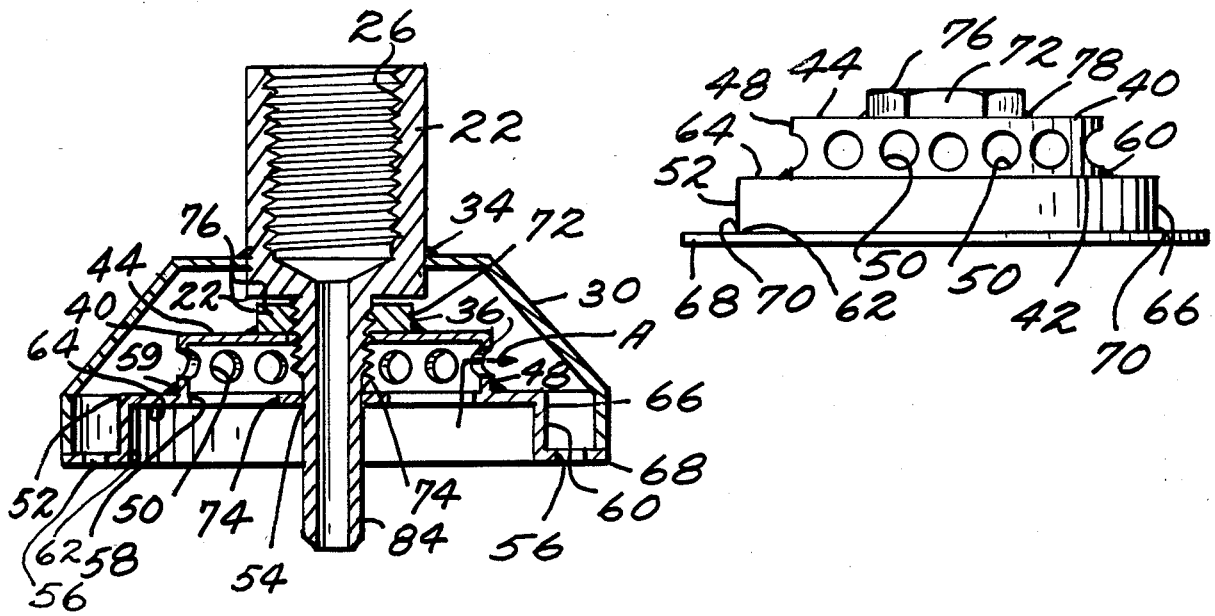

SHIELD FOR LIQUID SAMPLE CONTAINER

This invention relates to safety shields and more particularly to a safety shield for a liquid sample container.

It is a common practice in chemical plants to frequently obtain samples of liquid chemicals for analysis. Typically, a sample is obtained by draining a sample of the liquid into a sample container, such as a bottle. Often the liquid is highly corrosive or hazardous, and corrosive and hazardous vapors may often be given off from the liquid. The operator must wear protective clothing or equipment to protect himself from spilled or splashed liquid and to protect himself from escaping vapors.

It is, therefore, an object of the present invention to provide a safety shield for a liquid sample container which prevents accidental exposure of personnel to liquid and gaseous chemicals during sampling.

Another object is to provide such a safety shield which protects the operator from vapors displaced from the container and which protects the operator against sudden pressure changes in the sample container during the sampling process.

A further object of the invention is the provision of such a safety shield which helps reduce moisture accumulation in the sample container during the sampling process by providing a container cover.

Still another object is to provide such a safety shield which allows the sample container to be held firmly in place by the operator during the sampling process.

Yet another object of the present invention is the provision of such a shield which is compact and durable and which requires little or no maintenance.

A still further object is to provide such a safety shield wherein the nozzle is self-draining to reduce residue retention.

Another object is to provide such a safety shield which provides for continuous vapor venting.

Still another object is to provide a safety shield which is simple to install and which can withstand extreme temperature changes.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

To achieve these and other objects the present invention provides a safety shield for a liquid sample container, the shield comprising a nozzle adapted to be connected in fluid communication with a source of the liquid, a housing defining a lower open end and in operative relationship with the nozzle for partially enclosing the nozzle, and means in operative relationship with the nozzle and with the housing for directing in a downward direction any of the liquid splashed or overflowed from the container and any vapors from the liquid.

The accompanying drawings, which are incorporated in and constitute a part of this specification, illustrate an example of a preferred embodiment of the invention and, together with the description, serve to explain the principles of the invention.

FIG. 4 is a cross-sectional view of the safety shield taken along the line 4—4 in FIG. 2 and looking in the direction of the arrows;

FIG. 5 is an elevation view of that portion of the safety shield which, in cooperation with the housing, directs in a downward direction any liquid splashed or overflowed from a sample container and any vapors from the liquid; and FIG. 6 is a fragmentary perspective view of the safety shield showing the path of travel A of downwardly directed liquid and vapors.

Figure 1:
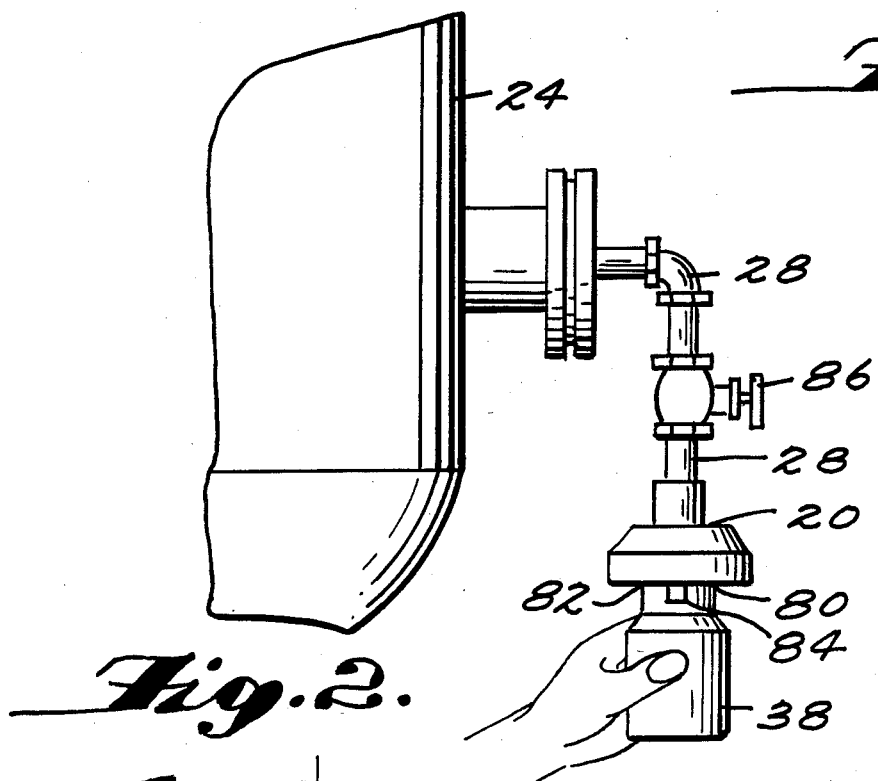
FIG. 1 is a fragmentary elevation view showing the safety shield connected to an outlet of a liquid source or tank.
Figure 2:
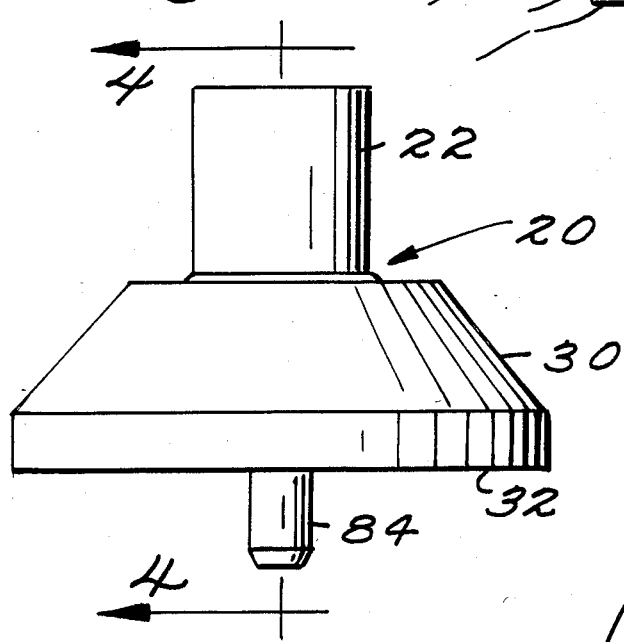
FIG. 2 is an elevation view of the safety shield.
Figure 3:
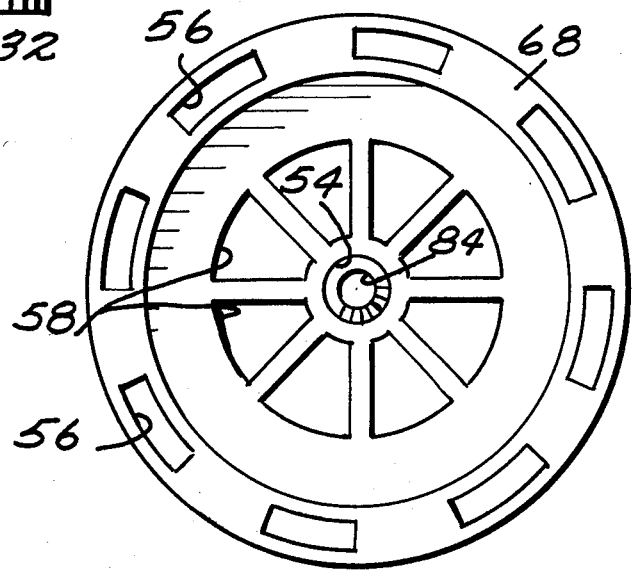
FIG. 3 is a bottom plan view of the safety shield.

With reference now to the drawings, wherein like reference characters designate like or corresponding parts throughout the several views, there is shown a safety shield 20 in accordance with this invention. A nozzle 22 is provided which is adapted to be connected in fluid communication with a line, tank or other source 24 of the liquid to be sampled. As illustrated in FIG. 4, nozzle 22 can be drilled and tapped for a standard size pipe thread, and interior threads 26 threadedly engage a sampling line 28 (FIG. 1) from liquid source 24.

Shield 20 also includes a housing 30 defining a lower open end 32 connected at 34 (FIG. 4) with nozzle 22 and partially enclosing the nozzle. Means 36 are provided in operative relationship with nozzle 22 and with housing 30 for directing in a downward direction any of the liquid splashed or overflowed from container 38 and any vapors from the liquid.

Directing means 36 include a first cylindrically-shaped member 40 having a first predetermined diameter and defining a first lower open end 42. Member 40 also includes a first upper closed end 44 having a first opening 46 therein and a first sidewall 48 projecting downwardly from upper end 44 and defining a plurality of second openings 50.

Directing means 36 also include a second member 52 defining a central opening 54 and a plurality of third openings 56 located between housing 30 and sidewall 48. Second member 52 further defines a plurality of fourth openings 58 located between central opening 54 and sidewall 48. In accordance with the invention, second member 52 is connected to sidewall 48 by a weld 59 or other conventional fastening means, and second member 52 extends substantially across open end 32 of housing 30.

More specifically, second member 52 includes a second cylindrically-shaped member 60 having a second predetermined diameter greater than the diameter of first cylindrically-shaped member 40. Member 52 further includes a second lower open end 62, a second upper closed end 64 connected to first sidewall 48 at weld 59 and defining central opening 54. Closed end 64 further defines fourth opening 58, and a second sidewall 66 projects downwardly from closed end 64.

A ring-shaped member 68 is connected to and projects outwardly from the lower end of sidewall 66, and ring-shaped member 68 defines third openings 56 therein. Ring-shaped member 68 can be welded or otherwise connected to the lower end of sidewall 66 at 70 (FIG. 5).

In accordance with the invention, means 72 are provided in operative relationship with nozzle 22 and with first cylindrically-shaped member 40 for removeably attaching directing means 36 to the nozzle. Nozzle 22 defines exterior threads (FIG. 4) and attaching means 72 is a nut 76 of a size to be threadedly engaged onto exterior nozzle threads 74. Nut 76 is attached to first cylindrically-shaped member 40 by means of a weld 78 or other conventional fastening means.

Shield 20 is made from a durable metal which is resistent to highly corrosive and hazardous materials. As a result, the shield requires little or no maintenance and can withstand extreme temperature changes. If it is necessary to clean shield 20, the assembly which comprises directing means 36 can be easily removed from nozzle 22 by removing nut 76 from nozzle thread 74. Directing means assembly 36 can also be quickly and easily replaced onto nozzle 22.

In use, safety shield 20 is typically attached to a sampling line 28 (FIG. 1) by means of interior nozzle threads 26. The shield will normally be permanently attached to the sampling line, but the shield can be removed from the sampling line when necessary or desired.

When it is desired to take a sample of liquid from source 24, the operator manually places sampling container 38, with its edge portion 80 surrounding its open end 82, into contact with upper end 64 of cylindrically-shaped member 60. Lower portion 84 of nozzle 22 extends into sampling container 38 (FIG. 1), and the diameter of opening 82 of the container is smaller than the diameter of cylindrically-shaped member 60. As a result, the operator can hold container 38 firmly against closed end 64 during the sampling procedure, and openings 58 will be in fluid communication with the interior of sampling container 38.

When a sample is desired, container 38 is placed into position by the operator against closed end 64, as described. The operator then opens a conventional sampling valve 86 (FIG. 1) and the liquid to be sampled flows from liquid source 24 through sampling line 28, through nozzle 22 and into sampling container 38.

As sampling container 38 is filled with liquid, shield 20 prevents liquid from being splashed upwardly onto the operator. The liquid being sampled may also give off corrosive or hazardous vapors. These vapors are typically collected within container 38, and the vapors are displaced from the container as the container is filled with liquid. As the vapors are displaced from the container, they pass upwardly through openings 58 (FIG. 6). The vapors are then forced out through openings 50, as shown by path A in FIG. 4. Housing 30 in cooperation with second member 52 then directs the vapors in a downward direction through opening 56 and to the atmosphere (FIG. 6). The displaced vapors are forced out through safety shield 20 in a downward direction and away from the face of the operator. This is in marked contrast to conventional sampling devices and arrangements wherein the displaced vapors are forced immediately upwardly to endanger the operator.

It is often the case that sampling of chemicals occurs outdoors. Safety shield 20 and housing 30 protect sampling container 38 and prevent rain or other moisture from being mixed with the liquid sample. Sudden pressure changes occurring within liquid source 24, which may result in splashing of the liquid as it is being sampled, often cause splashing of the liquid onto the operator during the sampling process. The safety shield of this invention prevents the liquid from being splashed upwardly into the face or onto the upper body of the operator during sampling. The shield of this invention also provides for continuous vapor venting away from the operator's face as previously described, and nozzle 22 is self draining to reduce residue retention.

The invention in its broader aspects is not limited to the specific details shown and described, and departures may be made from such details without departing from the principles of the invention and without sacrificing its chief advantages.

What is claimed:

1. A safety shield for a liquid sample container, said shield comprising:
   a nozzle adapted to be connected in fluid communication with a source of said liquid;
   a housing defining a lower open end and in operative relationship with said nozzle for partially enclosing said nozzle; and
   means in operative relationship with said nozzle and with said housing for directing in a downward direction any of said liquid splashed or overflowed from said container and any vapors from said liquid.

2. A shield as in claim 1 wherein said directing means comprise:
   a first cylindrically-shaped member having a first predetermined diameter and defining a first lower open end, a first upper closed end having a first opening therein, and a first sidewall projecting downwardly from said upper end and defining a plurality of second openings; and
   a second member defining a central opening and a plurality of third and fourth openings, said second member connected to said first sidewall and extending substantially across said housing open end.

3. A shield as in claim 2 wherein said third openings are located between said housing and said first sidewall.

4. A shield as in claim 3 wherein said fourth openings are located between said central opening and said first sidewall.

5. A shield as in claim 4 wherein said second member includes:
   a second cylindrically-shaped member having a second predetermined diameter and further including a second lower open end, a second upper closed end connected to said first sidewall and defining said central opening and said fourth openings, and a second sidewall projecting downwardly from said second upper closed end; and a ring-shaped member connected to and projecting outwardly from said second sidewall, said ring-shaped member further defining said third openings.

6. A shield as in claim 5 further including means in operative relationship with said nozzle and with said first cylindrically-shaped member for removably attaching said directing means to said nozzle.

7. A shield as in claim 6 wherein said second predetermined diameter is greater than said first predetermined diameter.

8. A shield as in claim 7 wherein said second predetermined diameter is greater than the largest dimension of the opening of said sample container.

9. A shield as in claim 8 wherein said nozzle defines exterior threads for receiving said attaching means.

10. A shield as in claim 9 wherein said attaching means is a nut attached to said first cylindrically-shaped member and adapted to threadedly engage said exterior threads.

11. A shield as in claim 10 wherein said nozzle further includes interior threads for threadedly engaging a sampling line from said liquid source.

* * * * *